(12) United States Patent
Abe (10) Patent No.: US 9,809,705 B2
(45) Date of Patent: *Nov. 7, 2017

(54) RESIN BEADS, METHOD FOR MANUFACTURING RESIN BEADS AND PRODUCT INCLUDING RESIN BEADS

(71) Applicant: DAINICHISEIKA COLOR & CHEMICALS MFG. CO., LTD., Tokyo (JP)

(72) Inventor: Takashi Abe, Tokyo (JP)

(73) Assignee: DAINICHISEIKA COLOR & CHEMICALS MFG. CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/305,571

(22) PCT Filed: Jul. 3, 2015

(86) PCT No.: PCT/JP2015/069234
§ 371 (c)(1),
(2) Date: Oct. 20, 2016

(87) PCT Pub. No.: WO2016/006540
PCT Pub. Date: Jan. 14, 2016

(65) Prior Publication Data
US 2017/0044360 A1   Feb. 16, 2017

(30) Foreign Application Priority Data

Jul. 9, 2014 (JP) .................................. 2014-141641

(51) Int. Cl.
| | | |
|---|---|---|
| C08L 33/10 | (2006.01) | |
| A61Q 1/00 | (2006.01) | |
| A61K 8/81 | (2006.01) | |
| A61K 8/89 | (2006.01) | |
| C08F 2/18 | (2006.01) | |
| A61K 8/893 | (2006.01) | |
| A61K 8/91 | (2006.01) | |
| A61Q 1/02 | (2006.01) | |
| C08L 35/02 | (2006.01) | |
| C08F 2/44 | (2006.01) | |
| C08K 5/54 | (2006.01) | |

(52) U.S. Cl.
CPC ................ *C08L 33/10* (2013.01); *A61K 8/81* (2013.01); *A61K 8/8152* (2013.01); *A61K 8/8164* (2013.01); *A61K 8/89* (2013.01); *A61K 8/893* (2013.01); *A61K 8/91* (2013.01); *A61Q 1/00* (2013.01); *A61Q 1/02* (2013.01); *C08F 2/18* (2013.01); *C08F 2/44* (2013.01); *C08K 5/54* (2013.01); *C08L 35/02* (2013.01); *A61K 2800/43* (2013.01); *A61K 2800/594* (2013.01); *C08L 2203/00* (2013.01)

(58) Field of Classification Search
CPC .................................. C08L 33/10; C08F 2/18
See application file for complete search history.

(56) References Cited

U.S. PATENT DOCUMENTS

2014/0017288 A1   1/2014   Matsushita

FOREIGN PATENT DOCUMENTS

| JP | 6173713 | 4/1986 |
|---|---|---|
| JP | 05-339125 | 12/1993 |
| JP | 0892524 | 4/1996 |
| JP | 08104772 | 4/1996 |
| JP | 9-227609 | 9/1997 |
| JP | 9-255705 | 9/1997 |
| JP | 2003073405 | 3/2003 |
| JP | 2004002728 | 1/2004 |
| JP | 2007100097 | 4/2007 |
| JP | 2009138034 | 6/2009 |
| JP | 2012072081 | 4/2012 |
| JP | 2013-053237 | 3/2013 |
| JP | 2013227535 | 11/2013 |
| WO | 0170826 | 9/2001 |
| WO | 2011121821 | 10/2011 |
| WO | 2012/102296 | 8/2012 |
| WO | 2013161098 | 10/2013 |

OTHER PUBLICATIONS

JP 2009 138034 Machine translation (2009).*
International Search Report, issued in the corresponding International Application No. PCT/JP2015/069234, dated Sep. 8, 2015, 5 pages.
Japanese Office Action, issued in the corresponding Japanese Patent application No. 2016-532909, 3 pages, dated Feb. 14, 2017.
Extended European Search Report, issued in the corresponding European patent application No. 15793062.9, dated Sep. 5, 2017, 6 pages.

* cited by examiner

*Primary Examiner* — Kuo-Liang Peng
(74) *Attorney, Agent, or Firm* — Hamre, Schumann, Mueller & Larson, P.C.

(57) ABSTRACT

The present invention provides resin beads that are capable of imparting stable water repellency and oil absorbency at a high level to products, and realizing good spreadability and excellent persistence of makeup without giving sticky feeling when added to, for example, cosmetic materials, the process for producing the resin beads, and various kinds of products using the resin beads and having excellent properties. Resin beads being resin particles obtained by subjecting a monomer mixture containing a plurality of monomers each having a copolymerizable functional group to suspension polymerization in a state where at least a non-polymerizable silicone compound is present, the resin particles each having a roughened surface, and a process for producing the resin beads, and various kinds of products each using the resin beads and each having excellent properties.

10 Claims, 1 Drawing Sheet

RESIN BEADS, METHOD FOR MANUFACTING RESIN BEADS AND PRODUCT INCLUDING RESIN BEADS

TECHNICAL FIELD

The present invention relates to resin beads being resin particles containing a non-polymerizable silicone compound, a process for producing the resin beads, and intended purposes of the resin beads. In more detail, the present invention relates to oil absorbent resin beads containing a non-polymerizable silicone compound inside in a fixed state, the non-polymerizable silicone being a functional material capable of imparting water repellency, wherein the surface of the resin particles is roughened. The present invention also relates to a process for producing the resin beads, and to utilization of the resin beads to products in the fields that need such functionality, such as, for example, cosmetics, dermal agents including ointments and medical patches, paints, shaped articles, films, coating agents, resin compositions, and other products.

BACKGROUND ART

Conventionally, resin beads have been used in various fields, such as a matting agent, a lubricant, and an antiblocking agent, because of the characteristics originating in the spherical shape. Furthermore, various kinds of resin powders (resin particles) have been used as makeup application in cosmetic materials in order to improve extensibility. However, these resin powders are liable to bleed due to water or sweat, thus there is a problem that makeup deterioration occurs when such bleed occurs, and when the resin powders are utilized in cosmetic materials, modification of the resin powders, or other methods has been conducted in order to maintain the adherence to skin, or other purposes.

As a method of modifying a resin powder, there is, for example, a method of applying hydrophobization treatment to a resin powder to improve the adherence to skin. As the method of applying hydrophobization treatment to a resin powder, a method of applying heat treatment with an oil agent to the surface of a powder, a method of baking a methyl hydrogen polysiloxane onto a powder, and so on are known. Furthermore, a proposal has been made on a powder the surface of which is coated with, for example, a silicone-acrylic-based graft copolymer in order to obtain a cosmetic material that achieves a higher functionality, that is excellent in adherence to skin and in feeling after use, that is rich in hydrophobicity, and that has a favorable persistence of makeup (see, Patent Literature 1).

Moreover, there is also a method of improving the adherence to skin by making a resin powder porous. As the method of making a resin powder porous, there is a method in which an oil phase containing a monomer and an organic solvent is subjected to suspension polymerization in an aqueous medium, and thereafter the organic solvent is distilled to obtain porous resin particles, and a proposal has been made to increase the oil absorption and improve persistence of makeup by making the resin particles porous in the manner as described above (see Patent Literature 2).

Moreover, in Patent Literature 3, it is described that, even though imparting water repellency, improving adherence to skin or the like, and securing compatibility with a coexisting oil agent are simultaneously required for silicone polymers that are often used in cosmetic materials, hydrophilicity is lost by introducing a long-chain alkyl group (hydrophobic group) in a silicone polymer in order to improve compatibility, on the other hand, hydrophobicity is lost by introducing a hydrophilic group in order to improve adherence, and thus it is difficult to solve the compatibility and the adherence simultaneously. Against the problem, it is described in Patent Literature 3 that, a copolymer obtained by copolymerizing four kinds of different monomer units each containing a particular amount of a silicone macromonomer having a particular structure can impart the water repellency, and at the same time, improve the adherence to skin or the like and the persistence of makeup.

CITATION LIST

Patent Literature

Patent Literature 1: Japanese Patent Laid-Open No. 5-339125

Patent Literature 2: Japanese Patent Laid-Open No. 2013-227535

Patent Literature 3: Japanese Patent Laid-Open No. 2012-072081

SUMMARY OF INVENTION

Technical Problem

However, in the method of baking a methyl hydrogen polysiloxane, there has been a problem that the surface treatment becomes ununiform depending on the kind of resin beads used or the reaction condition, and there has also been a problem that the resin is deteriorated by heat depending on the baking temperature. Moreover, according to studies conducted by the present inventor, in the method of coating the powder surface with the silicone-acrylic-based graft copolymer, which is proposed in Patent Literature 1, adsorption is not sufficient in some cases depending on the powder and the coating resin is peeled off from the powder surface in some cases depending on the kind of dispersion medium, such as an oil agent used together with the copolymer, and thus it has been difficult to say that the effect of modifying the resin powder is sufficient.

Moreover, according to studies conducted by the present inventor, when the porous resin powder proposed in Patent Literature 2 is used, for example, as a cosmetic material, the powder having a high specific surface area causes excessive water-absorbing action or moisture-absorbing action resulting in facilitation of sebum secretion, and makeup deterioration may occur. Thus, it has been difficult to say that the effect of modifying the resin powder is sufficient.

Moreover, Patent Literature 3 describes that utilization of a copolymer obtained by copolymerizing monomer units containing a polymerizable silicone macromonomer having a particular structure makes it possible to impart to cosmetic materials the characteristics of the silicone polymer of having less stickiness, extending smoothly, giving a light feeling after use, and being rich in water repellency. However, according to studies conducted by the present inventor, there have been problems described below. In the method of coating the surface of a resin powder with the copolymer obtained by copolymerizing the monomer units containing a polymerizable silicone macromonomer having a particular structure, adsorption is not sufficient in some cases depending on the powder as is the same as described above and the coating resin is peeled off from the powder surface in some cases depending on the kind of dispersion medium, such as an oil agent used together with the copolymer, and thus it has been difficult to say that the effect of modifying the resin powder is sufficient. Moreover, in the method of adding to cosmetic materials a copolymer obtained by copolymerizing monomer units containing a polymerizable silicone macromonomer having a particular structure, the copolymer also acts simultaneously to another powder being contained in the cosmetic materials and having a high specific surface area and therefore cannot be adsorbed to the surface of the resin beads in a sufficient amount in some cases, or the copolymer also acts to skin and therefore causes stretched feeling in some cases, and thus it has been difficult to say that the effect of improving a cosmetic material is sufficient.

From the above-described circumstances, the present inventor has recognized the usefulness of developing resin beads: that are capable of imparting water repellency and oil absorbency to products by using the resin beads as a raw material for the products; and that are capable of realizing a product that hardly causes makeup deterioration due to water or sweat, that exhibits good spreadability without giving sticky feeling when used as, for example, a raw material for cosmetic materials.

The present invention has been completed in consideration of such circumstances, and accordingly, an object of the present invention is to provide resin beads which are capable of imparting stable water repellency and oil absorbency at a high level to products when used, for example, in cosmetic materials by addition, and, as a result, which are capable of realizing good spreadability to skin and excellent persistence of makeup without giving sticky feeling. Another object of the present invention is to provide a process for producing the resin beads, and yet another object of the present invention is to provide various kinds of products using the resin beads and having excellent properties.

Solution to Problem

The objects are achieved by the present invention. That is to say, the present invention provides resin beads being resin particles obtained by subjecting a monomer mixture containing a plurality of monomers each having a copolymerizable functional group to suspension polymerization in a state where at least a non-polymerizable silicone compound is present, the resin particles each having a roughened surface.

The preferable embodiments of the resin beads include the following. That is to say, the amount of the non-polymerizable silicone compound that is present during the suspension polymerization is added in a ratio of 1.0 to 30 parts by mass to 100 parts by mass of the monomer mixture being a component for forming the resin; the non-polymerizable silicone compound is a silicone polymer; the non-polymerizable silicone compound is anyone selected from the group consisting of silicone-acrylic copolymers, polyether-modified silicones, polyether-alkyl-modified silicones, and silicone elastomers; the monomer having a copolymerizable functional group is a (meth)acrylate-based monomer; the monomer mixture contains a monomer having a plurality of copolymerizable functional groups in a content of 10% by mass or more; the monomer having a plurality of copolymerizable functional groups is a di(meth)acrylate; the suspension polymerization is conducted in a state where a pigment is further present; and the resin particles have a volume average particle diameter of 20 µm or less.

The present invention provides as another embodiment a resin beads production process for producing any of the above-described resin beads, including subjecting a polymerizable solution containing: a monomer mixture containing a plurality of monomers each having a copolymerizable functional group; a non-polymerizable silicone compound; a polymerization initiator; and, as necessary, a pigment to suspension polymerization in an aqueous phase containing a dispersion stabilizer dissolved therein, thereby obtaining resin beads each having at least water repellency and each having a roughened surface.

The present invention provides as yet another embodiment a water repellent and oil absorbent product containing resin beads and being any one selected from the group consisting of cosmetics, dermal agents, paints, shaped articles, films, coating agents, and resin compositions, wherein the resin beads are any of the resin beads described above.

Advantageous Effects of Invention

Figure 1:
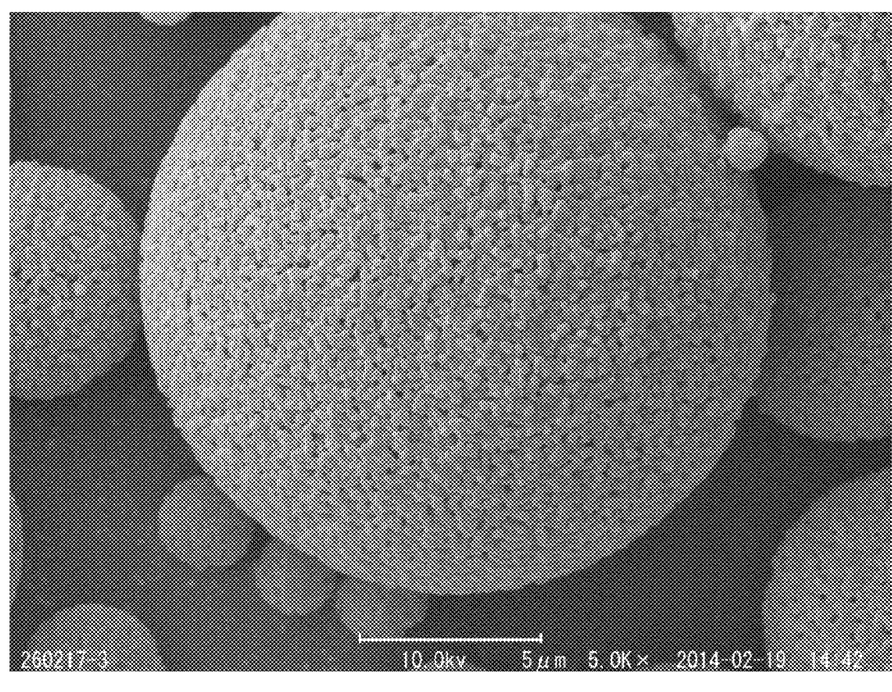
FIG. 1 shows an electron micrograph taken when a surface state of resin particles in resin beads of Example 1 was observed.

According to the present invention, because the resin beads are obtained by subjecting a monomer mixture containing a plurality of monomers each having a copolymerizable functional group, such as (meth)acrylate-based monomers, to suspension polymerization in a state where a non-polymerizable silicone compound is present, the non-polymerizable silicone compound is fixed inside the resin beads, and therefore when the resin beads are added to a product, sufficient water repellency is stably imparted to the product, thereby allowing the product to have properties that have never been achieved so far. Further, non-uniformity occurs at the surface of the resin powders from the difference in affinity to water between a resin portion that constitutes the resin beads, such as an acrylic resin, and the non-polymerizable silicone compound, the surface of the resin particles is roughened to increase the specific surface area as shown in FIG. 1, and therefore the resin beads have an increased oil absorption to become resin beads having excellent oil absorbency together with the water repellency. Thus, the resin beads according to the present invention, when used in cosmetic materials, etc., can realize sufficient water repellency and oil-absorbing effect stably and simultaneously, and can achieve excellent persistence of makeup. Namely, remarkable effects are obtained by applying the resin beads according to the present invention to cosmetic materials, etc.

DESCRIPTION OF EMBODIMENTS

Hereinafter, the present invention will be described in detail giving preferable embodiments according to the present invention. The present inventor has conducted various studies in order to realize resin beads excellent in persistence of makeup to newly find resin beads which contain a non-polymerizable silicone compound in a fixed state inside of the resin beads and in which the surface of the resin particles is roughened. The present inventor has reached the present invention by finding that utilization of the resin beads can realize excellent water repellency and oil absorbency (oil-absorbing effect) stably and simultaneously, and, when the resin beads are utilized in, for example, cosmetic materials, makeup deterioration due to water or body fat contained in sweat or the like can be reduced, thereby making it possible to solve the problems of the conventional technologies completely.

The resin beads according to the present invention are obtained by subjecting a monomer mixture containing a plurality of monomers each having a copolymerizable functional group to suspension polymerization in a state where at least a non-polymerizable silicone compound is present. The non-polymerizable silicone compound that constitutes the resin beads according to the present invention is not particularly limited as long as the silicone compound is non-polymerizable, and any of publicly known non-polymerizable silicone compounds can be used. For example, a non-polymerizable silicone compound that is suitable for cosmetic materials, dermal agents such as ointments and medical patches, paints, shaped articles, films, coating agents, or resin compositions may appropriately be used in consideration of the purpose of use. Non-polymerizable silicones that are used as a raw material for cosmetic materials are particularly suitable.

It is preferable that the non-polymerizable silicone compound for use in the present invention is a silicone polymer. Specific examples of the silicon polymer include the following. The examples include: modified silicones modified with various kinds of organic groups, such as polyether-modified silicones, polyester-modified silicones, acrylic modified silicones, polyether ester-modified silicones, polyether alkyl-modified silicones, polyether acrylic modified silicones, polyester acrylic modified silicones, polyglycerin-modified silicones, polyglycerin alkyl-modified silicones, phenyl-modified silicones, amino-modified silicones, carbinol-modified silicones, polyalkoxy-modified silicones, amino polyether-modified silicones, amide alkyl-modified silicones, aminoglycol-modified silicones, aminophenyl-modified silicones, polyether silicone/alkyl-comodified silicones, polyglycerin silicone/alkyl-comodified silicones and alkyl silicone comodified silicones; and polymers such as silicone-acrylic copolymers, silicone elastomers, trimethylsiloxysilicate-based silicones (silicone oils having a crosslinked structure), thermally denatured silicones, and polymeric silicones. Moreover, the structures of these non-polymerizable silicone compounds may be linear, branched, or cyclic, or these non-polymerizable silicone compounds may be highly polymerized, may have a crosslinked structure, or may be produced through graft polymerization. These non-polymerizable silicone compounds may be used alone or in combination of two or more. Furthermore, according to studies conducted by the present inventor, publicly known non-polymerizable silicone compounds excellent in applicability to cosmetic materials, such as silicone-acrylic copolymer-based silicones, polyether-modified silicones, polyether alkyl-modified silicones, and silicone elastomer-based silicones can be used more suitably among silicone compounds although the usability depends on the intended purpose.

The resin beads according to the present invention are resin particles (a copolymer) obtained by subjecting a monomer mixture containing a plurality of monomers each having a copolymerizable functional group to suspension polymerization in a state where at least the non-polymerizable silicone compound as described above is present, the resin particles each at least having a roughened surface. The resin component that constitutes the resin beads according to the present invention is not particularly limited, and any of publicly known resins can be used. For example, a resin that is suitable for cosmetic materials, dermal agents, paints, shaped articles, films, coating agents, or resin compositions may appropriately be used in consideration of the purpose of use. Specific examples of the resin include (meth)acrylate-based resins, styrene-based resins, olefin-based resins, polyester-based resins, polyurethane-based resins, poly(thio)ether-based resins, polysulfone-based resins, polyimide-based resins, polycarbonate-based resins, polyamide-based resins, epoxy-based resins, phenol-based resins, melamine-based resins, ultraviolet ray-curable resins, polymers derived from natural products, thermally denatured silicone polymers, and thermoplastic elastomers.

Accordingly, the resin component of the resin beads according to the present invention may be any of polymers obtained by selecting a plurality of monomers for forming the above-described resin, the monomers each having a copolymerizable functional group, and then subjecting the monomers in combination to polymerization. Examples of more suitable monomers for use in the present invention having a copolymerizable functional group include multifunctional monomers and crosslinkable monomers each having a plurality of copolymerizable functional groups. The details of these monomers will be mentioned later. Moreover, according to studies conducted by the present inventor, monomers, such as (meth)acrylate, for forming acrylic-based resins that are excellent in applicability to cosmetic materials, such as transparency, are more preferable among the monomers having a copolymerizable functional group, although the usability depends on the intended purpose. Specifically, publicly known acrylic-based or methacrylic-based monomers can suitably be used, and among others, methacrylic-based monomers can be used more suitably. It is to be noted herein that the (meth)acrylate in the present specification means methacrylate or acrylate. For example, methacrylates such as lauryl methacrylate can suitably be used.

According to studies conducted by the present inventor, it is preferable that the component for forming the resin that constitutes the resin beads according to the present invention is constituted so as to contain 10% by mass or more, further preferably 20% by mass or more of a monomer having a plurality of copolymerizable functional groups in all the monomers used. That is to say, by constituting the component as such, the resin beads formed through suspension polymerization contains the non-polymerizable silicone compound inside in a fixed state and the property of inhibiting the transfer of the non-polymerizable silicone compound in the resin is more improved. Therefore, with the resin beads used in, for example, cosmetic materials, a more uniform and favorable water repellent effect can be obtained, and the effect can be maintained more stably.

Examples of the monomer suitably used in the present invention and having a plurality of copolymerizable functional groups include copolymerizable multifunctional monomers and crosslinkable monomers, which are described below. As the copolymerizable multifunctional monomer or the crosslinkable monomer, general copolymerizable monomers containing a double bond adaptable to copolymerization are used. Examples of the monomer that is suitable for the present invention and is suitable for crosslinking include: (poly)ethylene glycol di(meth)acrylates such as ethylene glycol di(meth)acrylate, diethylene glycol di(meth)acrylate, and triethylene glycol di(meth)acrylate; bifunctional aliphatic (meth)acrylates such as dipropylene glycol di(meth)acrylate, tripropylene glycol di(meth)acrylate, tetraethylene glycol di(meth)acrylate, butanediol di(meth)acrylate, hexanediol di(meth)acrylate, and nonanediol di(meth)acrylate; and bifunctional alicyclic or aromatic (meth)acrylates such as tricyclodecane dimethanol di(meth)

acrylate, modified bisphenol A di(meth)acrylate, and bisphenol A diglycidyl ether di(meth)acrylate. Among them, it is preferable to use a bifunctional aliphatic (meth)acrylate such as a (poly)ethylene glycol di(meth)acrylate or hexanediol di(meth)acrylate, and further it is more preferable to use a bifunctional aliphatic methacrylate such as a (poly)ethylene glycol dimethacrylate or hexanediol dimethacrylate.

Moreover, examples of the monomer include: trifunctional (meth)acrylates such as pentaerythritol tri(meth)acrylate, trimethylolpropane tri(meth)acrylate, trimethylolpropane ethoxy tri(meth)acrylate, and glycerin propoxy tri(meth)acrylate; tetrafunctional (meth)acrylates such as pentaerythritol tetra(meth)acrylate, pentaerythritol ethoxy tetra(meth)acrylate, and ditrimethylolpropane tetra(meth)acrylate; hexafunctional (meth)acrylates such as dipentaerythritol hexa(meth)acrylate; and (meth)acrylates such as derivatives of these acrylates; oxetanes such as xylylene bisoxetane, and 3-ethyl-3[[(3-ethyloxetane-3-yl)methoxy]methyl] oxetane; and furthermore, (meth)acrylate-modified compounds such as urethane di(meth)acrylate, urethane tri(meth)acrylate, polyester di(meth)acrylates, and polyester tri(meth)acrylates.

Moreover, according to studies conducted by the present inventor, it is preferable that the resin beads according to the present invention containing the resin component obtained by polymerizing the monomers as described above contain the non-polymerizable silicone compound in a range described below relative to the resin component. That is to say, it is preferable that the resin beads according to the present invention contain the non-polymerizable silicone compound used in a ratio of 1.0 to 30 parts by mass relative to 100 parts by mass of the monomer mixture being a component for forming the resin. It is not preferable that the ratio is less than 1.0 parts by mass because the extent of the exhibition of water repellent effect or surface-roughening effect becomes small in some cases, and it is not preferable that the ratio exceeds 30 parts by mass because a remarkable effect cannot be expected despite an increase in the amount used and the resin beads are inferior in economic efficiency in some cases. It is preferable that the resin beads according to the present invention contains the non-polymerizable silicone compound used in a ratio of 1.0 to 25 parts by mass, and further 1.0 to 20 parts by mass relative to 100 parts by mass of the monomer being the component for forming the resin although the preferable amount depends on the intended purpose of the resin beads.

Moreover, according to studies conducted by the present inventor, the resin beads according to the present invention containing the resin component and the non-polymerizable silicone compound as essential constituents may contain a pigment in addition to these components depending on the intended purpose. Specifically, resin beads containing a pigment can be prepared by conducting suspension polymerization in a state where the pigment is present in addition to the non-polymerizable silicone compound. Examples of the pigment for use in preparing such resin beads include: metal oxides such as titanium dioxide, zinc oxide, Bengal red, yellow iron oxide, and black iron oxide; Yellow No. 4, Red No. 202 and Blue No. 1 each being the Japanese name of a certified color; and carbon blacks. Moreover, the resin beads may contain an extender such as mica, talc, kaolin, or calcium carbonate, or a surface active agent or dispersant that disperses the pigment. Furthermore, the resin beads may contain an ultraviolet-absorbing component, and examples of the ultraviolet-absorbing component include fine particles of titanium dioxide, fine particles of zinc oxide, cinnamic acid-based ultraviolet absorbers and dibenzoylmethane-based ultraviolet absorbers.

Moreover, it is preferable that the resin beads according to the present invention containing these constituents are fine particles having a volume average particle diameter within a range of 20 μm or less, more preferably having a volume average particle diameter within a range of 15 μm or less. When the volume average particle diameter falls within the range, the resin beads according to the present invention can effectively exhibit slipperiness and a soft focus property each being a property required, for example, as resin beads for cosmetic materials.

The process for producing the resin beads according to the present invention includes subjecting a polymerizable solution containing: a monomer mixture containing a plurality of monomers each having a copolymerizable functional group; a non-polymerizable silicone compound; a polymerization initiator; and, as necessary, a pigment to suspension polymerization in an aqueous phase containing a dispersion stabilizer dissolved therein. By constituting the process as such, the resin particles exhibiting at least water repellency and having a roughened surface can stably be produced and resin beads according to the present invention having uniform and favorable water repellency and oil-absorbing effect can be obtained. It is to be noted that the "monomer mixture" specified in the present invention means that two or more monomers coexist during reaction, but, as will be described later, does not necessarily mean that a plurality of monomers are in a mixed state in advance. In the present invention, it is preferable to prepare an oil phase polymerizable solution for conducting suspension polymerization in an aqueous phase in the manner, for example, as described below to obtain the resin beads using the prepared oil phase polymerizable solution. First of all, the polymerizable solution to be an oil phase is prepared by adding and mixing, in advance, the monomer mixture, the non-polymerizable silicone compound, and the polymerization initiator, and a solvent as necessary. The resin beads according to the present invention containing the non-polymerizable silicone compound inside in a fixed state can stably and easily be obtained by subjecting the polymerizable solution thus prepared to suspension polymerization in the aqueous phase containing a dispersion stabilizer dissolved therein.

As the polymerization initiator for use in the above-described production process, any one of publicly known polymerization initiators may be used as long as the polymerization initiator can achieve the objects of the present invention. Specifically, the polymerization initiators as listed below can be used. Examples of the polymerization initiator include peroxide-based polymerization initiators such as a lauryl peroxide, a benzoyl peroxide, and t-butyl peroxy(2-ethylhexate) and azo compounds such as 2,2'-azobisisobutyronitrile, 2,2'-azobis(2,4-dimethylvarelonitrile), and alkyl esters of 2,2'-azobisisobutyric acid. These polymerization initiators may be used alone or in combination of two or more.

In the case where the organic solvent is used for the production process according to the present invention, any one of publicly known organic solvents can preferably be used. Examples of the organic solvent that can suitably be used in the present invention include the following compounds. For example, ester-based solvents such as ethyl acetate and butyl acetate, ketone-based solvents such as methyl ethyl ketone and methyl isobutyl ketone, alcohols such as n-butanol, ether-based solvents such as ethyl cellosolve, butyl cellosolve, and ethylene glycol diethyl ether, glycol ether-based solvents such as dipropylene glycol monomethyl ether, and glycol ester-based solvents such as propylene glycol monomethyl ether acetate can be used, though not being particularly limited thereto. These organic solvents may be used alone or in combination of two or more.

The resin beads can be made to have a porous structure having pores inside within a range that does not deviate from the gist of the present invention. As a process of producing the porous resin beads for use in this case, any of publicly known processes can preferably be used. In the case where an organic solvent is used in the production process, publicly known solvents can be used. As the organic solvent that can suitably be used in this case, for example, saturated aliphatic hydrocarbons such as n-hexane, n-octane, and n-dodecane in addition to the above-described organic solvents can also be used, however the organic solvent is not particularly limited. These organic solvents may be used alone or in combination of two or more.

The suspension polymerization in the process for producing resin beads according to the present invention is conducted by mixing, under stirring, the polymerization solution having the above-described constitution into an aqueous medium (aqueous phase) prepared by dissolving a dispersion stabilizer (protective colloid) in deionized water. In conducting the suspension polymerization, the droplet diameter of suspension liquid in the polymerizable solution may be adjusted as necessary with an emulsification apparatus such as a homogenizer. The droplet diameter of the suspension liquid in the polymerizable solution can easily be adjusted by adjusting shear force by changing the number of revolutions of a homogenizer or the like, and as a result, the particle diameter of the resin particles obtained by conducting the suspension polymerization can appropriately be adjusted.

It is preferable to set the kind and concentration of the dispersion stabilizer not to cause trouble such as breakdown or unification of droplets of the suspension liquid prepared with an emulsification apparatus such as a homogenizer during droplet adjustment, during transportation to a polymerization apparatus, or during polymerization process. Examples of the dispersion stabilizer that is suitably used in the present invention include water-soluble polymers such as methyl cellulose, polyvinyl alcohols, and sodium acrylate, and inorganic salts such as hydroxyapatite, tribasic calcium phosphate, and calcium carbonate. These dispersion stabilizers may be used alone or in combination of two or more.

The resin beads according to the present invention are obtained by, for example, heating the suspension liquid obtained in the manner as described above at a temperature of 60 to 80° C. for 3 to 10 hours to conduct suspension polymerization. Further, after removing the dispersion stabilizer and so on through a washing process, the resin beads are peptized and dispersed in deionized water or the like, dissolved substances are removed through the washing process again, washing is repeated if necessary, and thereafter the resultant mixture is dried. Particles obtained in an aggregated state are crushed to obtain powdery resin beads. The resin beads according to the present invention obtained in the manner as described above, having at least water repellency, and having a roughened surface can be utilized as a constituent material for cosmetic materials, dermal agents such as ointments and medical patches, paints, shaped articles, films, coating agents, and resin compositions. In Examples, description is made on the cases where the resin beads according to the present invention is used as a cosmetic material as application examples, however the present invention is not limited to the application examples.

EXAMPLES

Hereinafter, the present invention will be described in more detail giving Examples and Comparative Examples, however the present invention is not limited by the following Examples. In addition, "parts" or "%" below is based on mass.

In Examples and Comparative Examples, a partially saponified polyvinyl alcohol was used as a dispersion stabilizer constituting an aqueous phase of suspension polymerization and an azo compound was used as a polymerization initiator unless otherwise noted. Specifically, Poval 205 (trade name) being a partially saponified polyvinyl alcohol (hereinafter, abbreviated as "PVA") and manufactured by Kuraray Co., Ltd. was used as the dispersion stabilizer, and V-65 being 2,2'-azobis(2,4-dimethylvarelonitrile) and manufactured by Wako Pure Chemical Industries, Ltd. (hereinafter, abbreviated as "V-65") was used as the polymerization initiator.

Example 1 (Example of Production with Polymerizable Monomer Liquid Containing Non-Polymerizable Silicone-Acrylic Copolymer)

First of all, to a solution prepared in advance and obtained by dissolving 4 parts of V-65 in 200 parts of a polyethylene glycol dimethacrylate (trade name: NK 1G, manufactured by Shin-Nakamura Chemical Co., Ltd.), 200 parts of lauryl methacrylate (trade name: LMA, manufactured by Kao Corporation) and 28 parts of a non-polymerizable silicone-acrylic copolymer (trade name: KP-578, active ingredient of 100%, manufactured by Shin-Etsu Chemical Co., Ltd.) were added, and the resultant mixture was uniformly stirred and mixed to prepare a polymerizable monomer liquid. KP-578 used above is a graft copolymer containing an acrylic polymer and a dimethylpolysiloxane. The viscosity is 150 to 200 mPa·s at 25° C.

Subsequently, in another container, the polymerizable monomer liquid prepared above was added and mixed to an aqueous phase obtained by dissolving 80 parts of PVA as a dispersion stabilizer in 1600 parts of ion-exchanged water, and the resultant mixture was stirred with a dissolver at 2500 rpm for 5 minutes and then further stirred with a homogenizer at 8000 rpm for 5 minutes to obtain a uniform suspension liquid.

Subsequently, in a reaction can of a polymerization apparatus provided with a stirrer and a nitrogen gas-introducing pipe, the suspension liquid obtained above was charged and subjected to polymerization reaction at 70° C. for 6 hours continuously. After cooling, fine resin particles produced from the suspension liquid were filtered and washed. The resin beads thus obtained were re-peptized in ion-exchanged water, and then the fine particles were filtered from the suspension liquid and were washed. Further, the fine particles were dried and crushed to obtain resin beads containing a non-polymerizable silicone compound inside in a fixed state, and the resin beads were used as the resin beads of the present Example.

Example 2 (Example of Production with Polymerizable Monomer Liquid Containing Non-Polymerizable Polyether-Alkyl Co-Modified Silicone)

First of all, 200 parts of butyl methacrylate (manufactured by Mitsubishi Rayon Co., Ltd.), 80 parts of a non-polymerizable polyether-alkyl co-modified silicone (trade name: KSG-310, active ingredients of 25 to 35%, manufactured by Shin-Etsu Chemical Co., Ltd.), and a solution prepared in advance and obtained by dissolving 4 parts of V-65 in 20 parts of propylene glycol monomethyl ether acetate were added to 200 parts of hexanediol dimethacrylate (trade name: NK Ester HD-N, manufactured by Shin-Nakamura Chemical Co., Ltd.). The resultant mixture was then uniformly stirred and mixed to prepare a polymerizable monomer liquid. Subsequently, in another container, resin beads containing a non-polymerizable silicone compound inside were obtained by the same operations, such as washing after polymerization, as in Example 1 except that polymerization was conducted using an aqueous phase obtained by dissolving 88 parts of PVA as a dispersion stabilizer in 1600 parts of ion-exchanged water. The obtained resin beads were used as the resin beads of the present Example. KSG-310 used above is a mixture of mineral oil and 25 to 35% of a polyether-alkyl co-modified silicone and is a material that has been used for cosmetics.

Example 3 (Example of Production with Polymerizable Monomer Liquid Containing Non-Polymerizable Silicone Elastomer)

Resin Beads Containing a Non-Polymerizable Silicone Compound inside in a fixed state were obtained by the same operations as in Example 1 except that 320 parts of lauryl methacrylate (trade name: LMA, manufactured by Kao Corporation) and 100 parts of a non-polymerizable silicone elastomer (trade name: 9040 S. E. B., active ingredients of 15%, manufactured by Dow Corning Toray Co., Ltd.) were added to a solution prepared in advance and obtained by dissolving 4 parts of V-65 in 80 parts of hexanediol dimethacrylate (trade name: NK Ester HD-N, manufactured by Shin-Nakamura Chemical Co., Ltd.), and the resultant mixture was uniformly stirred and mixed to prepare a polymerizable monomer liquid. The obtained resin beads were used as the resin beads of the present Example. The silicone elastomer (trade name: 9040 S.E.B.) used above is a mixture of 12% of a dimethicone crosspolymer and 88% of cyclopentasiloxane.

Example 4 (Example of Production with Polymerizable Monomer Liquid Containing Non-Polymerizable Polyether-Alkyl Co-Modified Silicone)

Resin beads containing a non-polymerizable silicone compound inside were obtained by the same operations, such as washing after polymerization, as in Example 1 except that, first of all, 200 parts of butyl methacrylate (manufactured by Mitsubishi Rayon Co., Ltd.), 8 parts of a non-polymerizable polyether-alkyl co-modified silicone (trade name: KF-6038, active ingredients of 100%, manufactured by Shin-Etsu Chemical Co., Ltd.), and a solution prepared in advance and obtained by dissolving 4 parts of V-65 in 20 parts of propylene glycol monomethyl ether acetate were added to 200 parts of hexanediol dimethacrylate (trade name: NK Ester HD-N, manufactured by Shin-Nakamura Chemical Co., Ltd.), and the resultant mixture was uniformly stirred and mixed to prepare a polymerizable monomer liquid. The obtained resin beads were used as the resin beads of the present Example. The silicone copolymer used above is sold on the market as a polyether-alkyl co-modified silicone surface active agent (HLB=3.0) and is lauryl PEG-9 polydimethylsiloxyethyl dimethicone.

Example 5 (Example of Resin Beads Produced with Polymerizable Monomer Liquid Containing Non-Polymerizable Polyether-Modified Silicone)

Resin beads containing a non-polymerizable silicone compound inside in a fixed state were obtained by the same operations as in Example 1 except that, first of all, 200 parts of hexanediol dimethacrylate (trade name: NK Ester HD-N, manufactured by Shin-Nakamura Chemical Co., Ltd.) and 60 parts of a non-polymerizable polyether-modified silicone (trade name: KF-6016, active ingredients of 100%, manufactured by Shin-Etsu Chemical Co., Ltd.) were added to a solution prepared in advance and obtained by dissolving 4 parts of V-65 in 200 parts of a polyethylene glycol dimethacrylate (trade name: NK 1G, manufactured by Shin-Nakamura Chemical Co., Ltd.), and the resultant mixture was uniformly stirred and mixed to prepare a polymerizable monomer liquid. The obtained resin beads were used as the resin beads of the present Example. The silicone copolymer is sold on the market as a polyether-modified silicone surface active agent (HLB=4.5) and is PEG-9-methyl ether dimethicone.

Example 6 (Example of Porous Resin Beads Produced with Polymerizable Monomer Liquid Containing Non-Polymerizable Silicone-Acrylic Copolymer)

Porous resin beads containing a non-polymerizable silicone compound inside in a fixed state were obtained by the same operations as in Example 1 except that, first of all, 200 parts of lauryl methacrylate (trade name: LMA, manufactured by Kao Corporation), 36 parts of a non-polymerizable silicone-acrylic copolymer (trade name: KP-578, active ingredients of 100%, manufactured by Shin-Etsu Chemical Co., Ltd.), which was the same as the one used in Example 1, and 400 parts of propylene glycol monomethyl ether acetate were added to a solution prepared in advance and obtained by dissolving 4 parts of V-65 in 200 parts of a polyethylene glycol dimethacrylate (trade name: NK 1G, manufactured by Shin-Nakamura Chemical Co., Ltd.), and the resultant mixture was uniformly stirred and mixed to prepare a polymerizable monomer liquid. The obtained porous resin beads were used as the resin beads of the present Example. In this Example, an oil phase containing a monomer and propylene glycol monomethyl ether acetate being an organic solvent is subjected to suspension polymerization in an aqueous medium, and therefore the resin beads obtained becomes porous.

Example 7 (Example of Production with Titanium Dioxide-Dispersed Polymerizable Monomer Liquid Containing Silicone-Acrylic Copolymer)

Resin beads containing a non-polymerizable silicone compound and titanium dioxide inside were obtained by the same operations as in Example 1 except that, first of all, a dispersion liquid of titanium dioxide was prepared in advance by adding and dispersing 80 parts of titanium dioxide (trade name: TIPAQUE PFC-407, manufactured by Ishihara Sangyo Kaisha, Ltd.), 200 parts of lauryl methacrylate (trade name: LMA, manufactured by Kao Corporation), and 36 parts of a non-polymerizable silicone-acrylic copolymer (trade name: KP-578, active ingredients of 100%, manufactured by Shin-Etsu Chemical Co., Ltd.), which was the same as the one used in Example 1, and a solution prepared in advance and obtained by dissolving 4 parts of V-65 in 200 parts of a polyethylene glycol dimethacrylate (trade name: NK 1G, manufactured by Shin-Nakamura Chemical Co., Ltd.) was uniformly stirred and mixed with the dispersion liquid to prepare a polymerizable monomer liquid. The obtained resin beads were used as the resin beads of the present Example.

Comparative Example 1 (Example of Polymerizable Monomer Liquid Not Containing Silicone Compound Resin beads of the present Comparative Example were obtained by the same operations as in Example 1 except that 200 parts of lauryl methacrylate (trade name: LMA, manufactured by Kao Corporation) was added to a solution prepared in advance and obtained by dissolving 4 parts of V-65 in 200 parts of a polyethylene glycol dimethacrylate (trade name: NK 1G, manufactured by Shin-Nakamura Chemical Co., Ltd.), which was the same solution as used in Example 1, and the resultant mixture was uniformly stirred and mixed to prepare a polymerizable monomer liquid. The obtained resin beads do not contain a silicone compound.

Comparative Example 2 (Example of Applying Coating Treatment to Beads of Comparative Example 1 with Silicone Compound)

Into a Henschel mixer, 100 parts of the resin beads obtained in Comparative Example 1 were charged, then a solution prepared in advance and obtained by dissolving 7 parts of the silicone-acrylic copolymer (trade name: KP-578, active ingredients of 100%, manufactured by Shin-Etsu Chemical Co., Ltd.), which was the same as the one used in Example 1, in 7 parts of isopropyl alcohol was injected into the mixer, and the resultant mixture was uniformly stirred and mixed and thereafter dried and crushed to obtain resin beads of the present Comparative Example. The obtained resin beads contain a silicone compound that covers the surfaces of the resin beads.

Comparative Example 3 (Example of Porous Beads Produced with Polymerizable Monomer Liquid not Containing Silicone Compound Porous resin beads of the present Comparative Example were obtained by the same operations as in Example 4 except that 200 parts of lauryl methacrylate (trade name: LMA, manufactured by Kao Corporation) and 400 parts of propylene glycol monomethyl ether acetate were added to a solution prepared in advance and obtained by dissolving 4 parts of V-65 in 200 parts of a polyethylene glycol dimethacrylate (trade name: NK 1G, manufactured by Shin-Nakamura Chemical Co., Ltd.), which was the same solution as used in Example 4, and the resultant mixture was uniformly stirred and mixed to prepare a polymerizable monomer liquid. The obtained resin beads are porous similar to those of Example 4 but do not contain a silicone compound.

Comparative Example 4 (Example of Titanium Dioxide-Dispersed Polymerizable Monomer Liquid not Containing Silicone Compound Resin beads of the present Comparative Example were obtained by the same operations as in Example 1 except that, first of all, a dispersion liquid of titanium dioxide was prepared in advance by adding and dispersing 80 parts of titanium dioxide (trade name: PFC-407, manufactured by Ishihara Sangyo Kaisha, Ltd.) and 200 parts of lauryl methacrylate (trade name: LMA, manufactured by Kao Corporation), and a solution prepared in advance and obtained by dissolving 4 parts of V-65 in 200 parts of a polyethylene glycol dimethacrylate (trade name NK 1G, manufactured by Shin-Nakamura Chemical Co., Ltd.) was uniformly stirred and mixed with the dispersion liquid to prepare a polymerizable monomer liquid. The obtained resin beads are the same as those of Example 7 in that titanium dioxide was contained during suspension polymerization and the same resin composition was used, but does not contain a silicone compound.

<Evaluation>

The volume average particle diameter for resin beads of each of Examples and Comparative Examples was measured, and further, the water repellency, the oil absorption (oil absorbency), and the surface state of resin particles were each evaluated in the following manner.

(Measurement of Volume Average Particle Diameter)

The volume average particle diameter for resin beads of each of Examples 1 to 7 and Comparative Examples 1 to 4 was measured with a Coulter counter (manufactured by Beckman Coulter, Inc.). Obtained results are shown together in Table 1.

(Evaluation of Water Repellency)

The water repellency for resin beads of each of Examples 1 to 7 and Comparative Examples 1 to 4 was observed in the following manner and evaluated according to the following criteria. Specifically, 20 ml of ion-exchanged water was put in a 50 ml test tube, and 0.5 g of resin beads were added thereto and then lightly stirred with a spatula. Whether the resin beads were floating on the surface or not was observed after 1 day, and the water repellency was evaluated by the precipitation state of the resin beads. Evaluation was conducted according to the evaluation criteria in which the state where the resin beads were completely floating was ranked as A, the state where part of the resin beads precipitated was ranked as B, and the state where most of the resin beads precipitated was ranked as C. The results are shown together in Table 1.

(Measurement of Oil Absorption)

The oil absorption for resin beads of each of Examples 1 to 7 and Comparative Examples 1 to 4 was measured in the following manner to evaluate the oil absorbency. Specifically, a fatty acid triglyceride (trade name: COCONARD MT, manufactured by Kao Corporation) was gradually dropped into 5.0 g of resin beads of each of Examples and Comparative Examples and mixed with a spatula. The resin beads were gradually wetted as the dropping was continued, and the amount dropped (g) at the time when the resin beads gathered together to forma lump was defined as the oil absorption of the resin beads to evaluate the oil absorbency (oil-absorbing effect). The results are shown together in Table 1.

(Observation of Surface State of Resin Particles)

The surface state of resin particles in resin beads of each of Examples 1 to 7 and Comparative Examples 1 to 4 was observed with a scanning electron microscope (ERA-8000, manufactured by ELIONIX Inc.). According to the observation result with 5000 magnifications, the surface state is expressed as "smooth" when the surface of the resin particles is smooth, as "roughened surface" when the surface of the resin particles is roughened, as "pigments adsorbed" when the pigments cannot be contained inside the particles, and are adsorbed to and aggregated at the surface of the resin, or as "porous" when the surface of the resin particles is porous, and the results are shown together in Table 1. FIG. 1 shows an electron micrograph taken when the surface state of the resin particles in resin beads of Example 1. When the surface state of a resin particle is in a state where the surface is roughened as shown in FIG. 1, the surface state was defined as in a state where "a surface is roughened" specified in the present invention.

TABLE 1

Evaluation results of particle diameter, water repellency, oil absorption, and surface state of resin beads of Examples and Comparative Examples

|  | Silicone compound | | | Average | | | |
|---|---|---|---|---|---|---|---|
|  | Kind | Amount present (parts) | Amount of monomer having a plurality of functional groups | particle diameter (μm) | Surface state | Water repellency | Oil absorption (g) |
| Example 1 | Silicone-acrylic copolymer (KP-578) | 7.0 | 50% | 10.1 | Roughened surface | A | 4.7 |
| Example 2 | Polyether-alkyl-comodified silicone (KSG-310) | 5 to 7 | 50% | 9.7 | Roughened surface | A | 3.8 |
| Example 3 | Silicone elastomer (9040S) | 3.8 | 20% | 10.2 | Roughened surface | A | 3.6 |
| Example 4 | Polyether-alkyl-comodified silicone (KF-6038) | 2.0 | 50% | 8.5 | Roughened surface | A | 3.7 |
| Example 5 | Polyether-modified silicone (KF-6016) | 15.0 | 100% | 8.9 | Roughened surface | A | 4.6 |
| Example 6 | Silicone-acrylic copolymer (KP-578) | 9.0 | 50% | 9.6 | Roughened surface(porous) | A | 5.3 |
| Example 7 | Silicone-acrylic copolymer (KP-578 + TiO$_2$ contained) | 9.0 | 50% | 10.2 | Roughened surface | A | 4.6 |
| Comparative Example 1 | None | | 50% | 10.1 | Smooth | C | 2.1 |
| Comparative Example 2 | Surface covered by silicone-acrylic copolymer (KP-578) | Mixed afterwards 7.0 | 50% | 10.1 | Smooth | B | 2.1 |
| Comparative Example 3 | None | | 50% | 9.6 | Smooth (porous) | C | 4.1 |
| Comparative Example 4 | None (TiO$_2$ contained) | | 50% | 9.9 | Smooth (pigments adsorbed) | C | 2.5 |

(Use-1 in Cosmetic Materials)

Cosmetic materials-1 of Examples 8 to 13 and Comparative Examples 5 to 7 were produced by blending the resin beads of each of Examples 1 to 6 and Comparative Examples 1 to 3 and respective components shown in Table 2 in an amount blended as shown in Table 2, and usability thereof was evaluated. More specifically, the cosmetic materials were produced in the following manner. First of all, as described in Table 2, each of silicone-treated powders (mica, talc, fine particles of titanium oxide, and barium sulfate), which have conventionally been used, and resin beads of each of Examples and Comparative Examples were blended in an amount described in Table 2, and the resultant mixture was mixed until the mixture became uniform to prepare a powder mixture. A mixture prepared in advance by mixing vaseline, squalene, and glyceryl trioctanoate, each of which has conventionally been used as a raw material for cosmetic materials, was added to the powder mixture, and the resultant mixture was mixed until the mixture became uniform. Subsequently, the resultant mixture was filled in a container, and was subjected to press molding as necessary to obtain each of cosmetic materials-1 each containing different resin reads. The usability with respect to the items shown in Table 4 was evaluated according to the evaluation criteria shown in Table 4 using each of cosmetic materials-1 each containing different resin beads, and the results are also shown together in Table 4.

TABLE 2

Compositions of cosmetic materials-1 of Examples 8 to 13 and Comparative Examples 5 to 7

|  | Component | (parts by mass) Amount blended |
|---|---|---|
| Additional components | vaseline | 2.5 |
|  | squalene | 3.0 |
|  | glyceryl trioctanoate | 2.0 |
| Powder mixture | Silicone-treated mica | 40.0 |
|  | Silicone-treated talc | 33.0 |
|  | Fine particles of silicone-treated titanium oxide | 5.0 |
|  | Silicone-treated barium sulfate | 10.0 |
|  | Resin beads of each of Examples 1 to 6 and Comparative examples 1 to 3 | 4.5 |

(Use-2 in Cosmetic Materials)

Cosmetic materials-2 of Example 14 and Comparative Example 8 were produced by blending the resin beads of each of Example 7 and Comparative Example 4 and respective components shown in Table 3 in an amount as shown in Table 3, and usability thereof was evaluated. More specifically, the cosmetic materials-2 were produced in the following manner. First of all, the oil phase components described in Table 3 were mixed, a powder mixture obtained in advance by mixing the powder components described in Table 3 until the powder components became uniform was then mixed with the oil phase components, and the resultant mixture was dispersed with a disper. The water-soluble components described in Table 3 were then added therein under stirring to emulsify the resultant mixture, thereby obtaining each of cosmetic materials-2 each being an emulsified liquid foundation. AS for any of the components described in the table, the material that had conventionally been used as a raw material for cosmetics was used. The usability with respect to the items shown in Table 4 was evaluated according to the evaluation criteria shown in Table 4 using each of the obtained cosmetic materials-2, and the results are also shown together in Table 4.

TABLE 3

Compositions of cosmetic materials-2 of Example 14 and Comparative Example 8

| | Component | (parts by mass) Amount blended |
|---|---|---|
| Water-soluble components | Purified water | 42.0 |
| | Glycerin | 7.0 |
| Oil phase components | Silicone oil | 29.0 |
| | Ultraviolet protective agent | 2.0 |
| Powder components | Bengal red | 0.4 |
| | Yellow iron oxide | 1.5 |
| | Black iron oxide | 0.1 |
| | Sericite | 4.0 |
| | Resin beads of Example 7 or Comparative Example 4 | 16.0 |

TABLE 4

Evaluation results for cosmetic materials

| Resin beads | Example of cosmetic material | Spread-ability to skin | Fitness | Feeling without stickiness | Persistence of makeup |
|---|---|---|---|---|---|
| Example 1 | Example 8 | AA | AA | AA | AA |
| Example 2 | Example 9 | AA | AA | AA | AA |
| Example 3 | Example 10 | AA | AA | AA | AA |
| Example 4 | Example 11 | AA | AA | AA | AA |
| Example 5 | Example 12 | AA | AA | AA | AA |
| Example 6 | Example 13 | AA | AA | AA | AA |
| Example 7 | Example 14 | AA | AA | AA | AA |
| Comparative Example 1 | Comparative Example 5 | A | B | C | C |
| Comparative Example 2 | Comparative Example 6 | A | A | B | C |
| Comparative Example 3 | Comparative Example 7 | A | B | C | C |
| Comparative Example 4 | Comparative Example 8 | C | C | C | C |

(Evaluation result)
AA: Excellent,
A: Good,
B: Fair,
C: Poor (Evaluation Results)

When the resin beads of Examples 1 to 7 and the resin beads of Comparative Examples 1 to 4 were compared, it was able to be confirmed that, as shown in Table 1, the resin beads of any of Examples 1 to 7 were clearly more excellent in water repellency than the resin beads of Comparative Examples, and, further, that the resin beads of any of Examples 1 to 7 had oil absorption that was almost equal to the oil absorption of the porous resin beads of Comparative Example 3 and therefore were excellent in oil absorbency because the surfaces of the resin particles in the resin beads of Examples 1 to 7 were roughened (see FIG. 1). Moreover, each of the cosmetic materials of Examples 8 to 14 produced using the resin beads of Examples 1 to 7 respectively, when compared with the cosmetic materials of Comparative Examples 5 to 8 produced using the resin beads of Comparative Examples 1 to 4 respectively, gave less stickiness, and had lighter spreadability, more favorable fitness, and more favorable persistence of makeup. As a result, it was confirmed that a cosmetic material exhibiting a makeup deterioration-preventing effect can be obtained by using the resin beads of Examples according to the present invention. Furthermore, it was found that the resin beads according to the present invention, when used in a product, can impart stable water repellency and oil absorbency at a high level to the product also in dermal agents such as ointments and medical patches, paints, films, coating agents, and resin compositions in the same manner, and therefore were useful as a material that can impart functionality.

INDUSTRIAL APPLICABILITY

In the resin beads according to the present invention, a silicone compound is contained in the resin beads themselves, and the silicone compound is fixed inside the resin beads, and, besides, the surface of the resin beads is roughened. Therefore, the resin beads according to the present invention are useful when used in a product in that the product can realize stable water repellency and oil-absorbing effect simultaneously. Thus when the resin beads according to the present invention are used in, for example, cosmetic materials, products that have stable water repellency and oil absorbency and that achieve favorable persistence of makeup can be obtained. Accordingly, the resin beads according to the present invention are most suitable for use in the fields that need such properties and functions, such as, for example, cosmetic materials, dermal agents, paints, shaped articles, films, coating agents, and resin compositions, and use of the resin beads according to the present invention in a wide variety of intended purposes is expected.

The invention claimed is:
1. Resin beads being resin particles, each having a roughened surface,
   wherein the resin particles are a product of suspension polymerization of a monomer mixture comprising a plurality of monomers each having a copolymerizable functional group, in the presence of at least a non-polymerizable silicone compound, and
   the non-polymerizable silicone compound is at least one material selected from the group consisting of silicone-acrylic copolymers, polyether-modified silicones, polyether-alkyl-modified silicones, and silicone elastomers.
2. The resin beads according to claim 1,
   wherein an amount of the non-polymerizable silicone compound present in the suspension polymerization is at a ratio from 1.0 to 30 parts by mass relative to 100 parts by mass of the monomer mixture that is a component of forming resin of the resin particles.
3. The resin beads according to claim 1,
   wherein the non-polymerizable silicone compound is a silicone-acrylic copolymer.
4. The resin beads according to claim 1,
   wherein the monomer having a copolymerizable functional group is a (meth)acrylate-based monomer.
5. The resin beads according to claim 1,
   wherein the plurality of monomers each having a copolymerizable functional group comprises a monomer having a plurality of copolymerizable functional groups, and
   the monomer mixture comprises the monomer having a plurality of copolymerizable functional groups in a content of 10% by mass or more relative to the plurality of monomers each having a copolymerizable functional group in the monomer mixture.
6. The resin beads according to claim 5, wherein the monomer having a plurality of copolymerizable functional groups is a di(meth)acrylate.

7. The resin beads according to claim 1,
wherein the resin particles have a volume average particle diameter of 20 μm or less.

8. A resin beads production process for producing the resin beads according to claim 1, comprising:
subjecting a polymerizable solution comprising: the monomer mixture comprising:
the plurality of monomers each having a copolymerizable functional group;
the non-polymerizable silicone compound;
a polymerization initiator; and
optionally a pigment
to the suspension polymerization in an aqueous phase,
the aqueous phase comprises a dispersion stabilizer dissolved therein, thereby obtaining resin beads each having at least water repellency and the roughened surface.

9. A water repellent and oil absorbent product comprising: the resin beads according to claim 1 in at least one product selected from the group consisting of cosmetics, dermal agents, paints, shaped articles, films, coating agents, and resin compositions.

10. Resin beads, each having a roughened surface,
wherein the resin particles are a product of suspension polymerization of a monomer mixture comprising a plurality of monomers each having a copolymerizable functional group, in the presence of at least a non-polymerizable silicone compound, and
the suspension polymerization is conducted in a state where a pigment is further present.

* * * * *